(12) United States Patent
Tannenbaum

(10) Patent No.: US 11,465,088 B2
(45) Date of Patent: Oct. 11, 2022

(54) SYSTEM FOR SAMPLING, TESTING AND FILTERING AIR FOR CONTAMINANTS

(71) Applicant: Adam Benjamin Tannenbaum, Ashdod (IL)

(72) Inventor: Adam Benjamin Tannenbaum, Ashdod (IL)

( * ) Notice: Subject to any disclaimer, the term of this patent is extended or adjusted under 35 U.S.C. 154(b) by 199 days.

(21) Appl. No.: 16/922,380

(22) Filed: Jul. 7, 2020

(65) Prior Publication Data

US 2022/0008860 A1 Jan. 13, 2022

(51) Int. Cl.
| | | |
|---|---|---|
| *B01D 46/44* | (2006.01) | |
| *B08B 15/00* | (2006.01) | |
| *G01N 33/00* | (2006.01) | |
| *B01D 46/00* | (2022.01) | |
| *B01D 46/42* | (2006.01) | |
| *B01D 46/46* | (2006.01) | |

(52) U.S. Cl.
CPC ....... *B01D 46/442* (2013.01); *B01D 46/0028* (2013.01); *B01D 46/0043* (2013.01); *B01D 46/4245* (2013.01); *B01D 46/46* (2013.01); *B08B 15/002* (2013.01); *G01N 33/0031* (2013.01); *B01D 2279/65* (2013.01)

(58) Field of Classification Search
CPC ............ B01D 46/0028; B01D 46/0043; B01D 46/4245; B01D 46/442; B01D 46/46; B01D 2279/65; G01N 33/0031; B25J 15/0616; B08B 5/04; B08B 13/00; B08B 15/002; F24F 8/00; F24F 8/10; F24F 8/108; F24F 8/80; F24F 3/16; F24F 3/163; B23K 9/325; A47L 9/2805; A47L 9/281

See application file for complete search history.

(56) References Cited

U.S. PATENT DOCUMENTS

| | | | |
|---|---|---|---|
| 6,780,213 B2 * | 8/2004 | Chang ................ | B08B 15/00 55/385.2 |
| 9,180,547 B2 * | 11/2015 | Brenneke ............ | B23K 9/325 |
| 9,296,572 B2 | 3/2016 | Houghton et al. | |
| 9,895,462 B2 | 6/2018 | Law et al. | |
| 2009/0162255 A1 | 6/2009 | Chan et al. | |
| 2014/0109934 A1 * | 4/2014 | Lee ...................... | B08B 5/04 15/303 |
| 2019/0029486 A1 * | 1/2019 | Suvarna ............ | A47L 11/4061 |

FOREIGN PATENT DOCUMENTS

CA        2748583        6/2013

* cited by examiner

*Primary Examiner* — Gabriel E Gitman
(74) *Attorney, Agent, or Firm* — Robert Brownstein

(57) ABSTRACT

The invention herein disclosed is a system that supports sampling, testing and filtering of air in selected small volumes of air within a larger air pool.

10 Claims, 6 Drawing Sheets

601

SYSTEM FOR SAMPLING, TESTING AND FILTERING AIR FOR CONTAMINANTS

TECHNICAL FIELD

The invention is a system for detection and filtering of air contaminants.

BACKGROUND OF INVENTION

Air is a mixture of gaseous atoms and molecules, primarily nitrogen (approximately 79 percent) and oxygen (approximately 21 percent). Humans draw air into their lungs in order to obtain oxygen for use by various cells. Air may also contain small particles, other gaseous atoms and molecules, and biologic pathogens. These are considered contaminants and may cause harm to humans who breathe in air containing such.

Most manufacturing facilities, restaurants, and places where large groups of humans or animals may congregate have systems which draw in air, filter it, and either warm or cool it before returning it to the original pool of air. Some systems provide a steady ventilation wherein they remove air from the interior and replace it with air from the outside.

In nearly all such cases, the air intake and exhaust subsystems are contained in walls and ceilings. Thus, the pool of air is drawn in by one or a few intake subsystems causing a relatively slow air current in which air farthest away from the intake may take a relatively long time to be drawn into the intake system, or may remain behind.

Like in water, a localized disturbance in air gradually disperses through the pool of air. Thus, a localized release of contaminants in one place in a pool of air is initially contained in a small sub-volume of air and will disperse over time. If the contaminant can be selectively drawn in, before it can disperse, it may be drawn in sufficiently to reduce the contamination in a relatively short amount of time. However, at present, there are no systems that provide sampling, testing and filtering of air in selective sub-volumes in an air pool. Thus, determining that contamination has occurred, and then remediating that contamination is largely hit and miss.

BRIEF DESCRIPTION OF INVENTION

The invention herein disclosed and claimed is a system that selectively samples small volumes of air in an air volume zone (a volume of air within a larger pool of air), then tests the air for contaminants, and if detected, diverts the air flow through a filtering subsystem that removes the contaminants prior to releasing the air back into the air volume zone.

A key portion of the system is its flexible, ribbed hose which can be positioned virtually anywhere within an air volume zone to quickly draw in air from a selected sub-volume (a portion of air within an air volume zone), test it for contaminants, and filter it in the event that contaminants are detected.

As the flexible, ribbed hose is moved around an air volume zone, it may detect a contamination disturbance before it has a chance to disperse such that filtering can remove most of the contamination in that sub-volume before moving on to test other sub-volumes. The air release will be from a secondary pipe that keeps exhausted air removed from active sampling positions.

Multiple systems can be linked together within an air volume zone so that sampling, testing and filtering is done in parallel to reduce the time for sampling the air volume zone. Within a facility, containing several air volume zones and several systems, the individual systems convey near real-time data to a server that is capable of redirecting any individual system's flexible, ribbed hose to a specific location within an air volume zone. In essence, the server can orchestrate the actions of one or more systems to more quickly sample, test and filter at predetermined sub-volumes within air volume zones.

For example, in a factory where one or a few assembly stations are involved in a process that may produce toxic gaseous output or troublesome particulates, the system or systems assigned to that area's air volume zones can optimize the sample, test and filter process such that contamination remains localized and is quickly remediated.

DETAILED DESCRIPTION OF INVENTION

The system herein disclosed and claimed allows selective sampling, testing and filtering of sub-volumes of air within a larger air volume zone.

Figure 1:
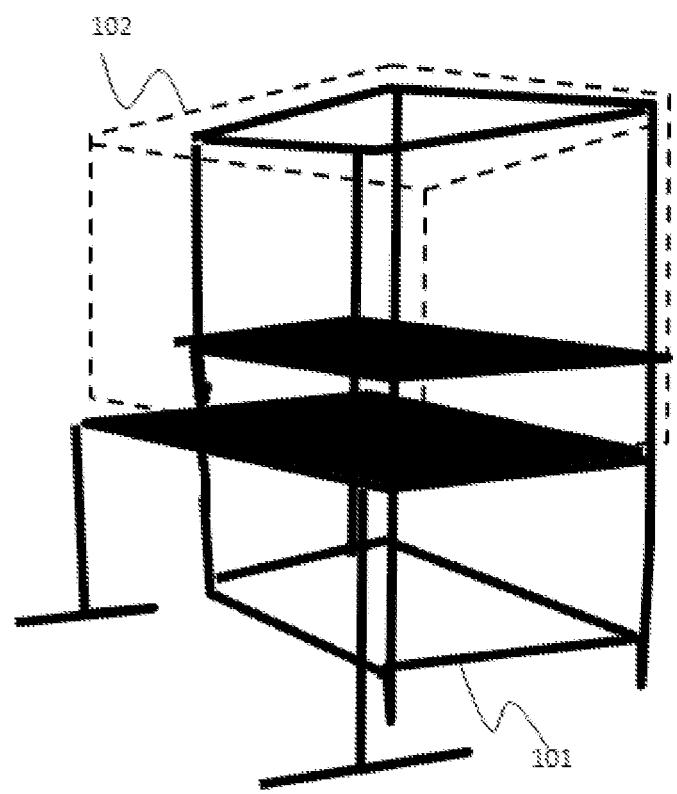
FIG. 1 depicts an air volume zone by a manufacturing assembly position.

FIG. 1 shows a manufacturing assembly position (101) and an air volume zone (102). Although the figure shows a manufacturing example, it could also be a cooking area in a restaurant, a lab area in a healthcare facility, and the like.

Figure 2:
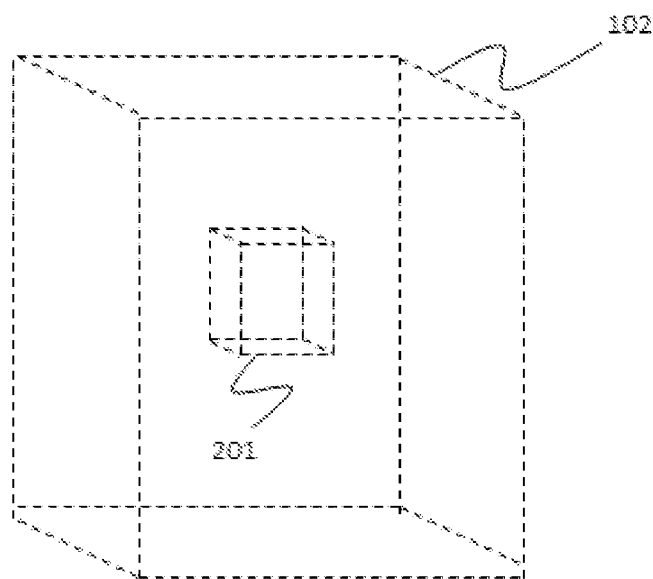
FIG. 2 depicts a sub-volume within an air volume zone.

FIG. 2 depicts a sub-volume (201) within an air volume zone (102). For example, the air volume zone may be a four-by-four-by-four foot cube of air (64 cubic feet) and the sub-volume may be a one-by-one-by-one foot cube of air (1 cubic foot) within that air volume zone.

Figure 3:
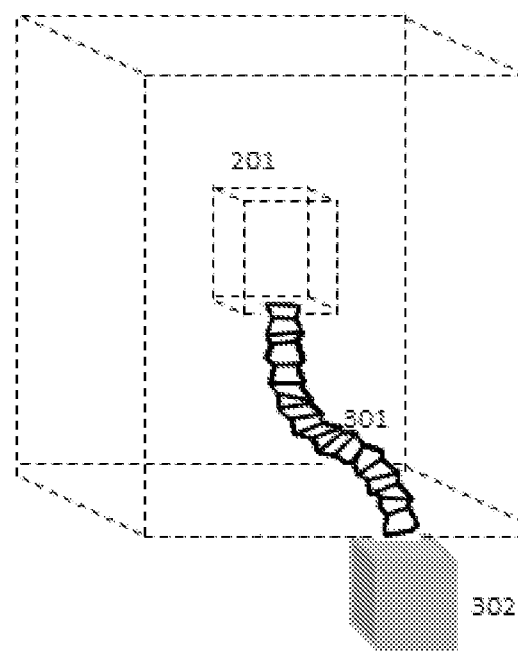
FIG. 3 depicts an embodiment of the invention sampling air in a sub-volume.

In FIG. 3, an embodiment of the invention system (301 and 302) sits within an air volume zone and the position of its flexible, ribbed hose (301) provides sampling of sub-volume 201. Many subsystems are contained in 302 which support sampling, testing and filtering of sub-volumes of air.

Figure 4:
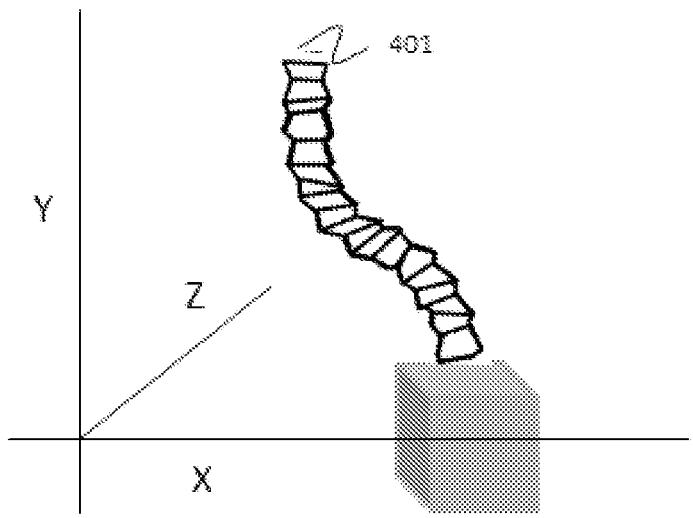
FIG. 4 illustrates a position-detection device in the tip of a flexible, ribbed hose that is used to provide three-dimension location data.

As shown in FIG. 4, a key element of the invention system is the flexible, ribbed hose, which is moved around within the air volume zone, and which contains a position-detection device at its tip (401) that provides three-dimensional position data for closed-loop positioning control. Like a gooseneck portion of a lamp, the flexible, ribbed hose allows the hose tip to be moved essentially anywhere within its air volume zone, and once positioned, to remain in that position while drawing in air from a sub-volume for testing and possible filtering.

Figure 5:
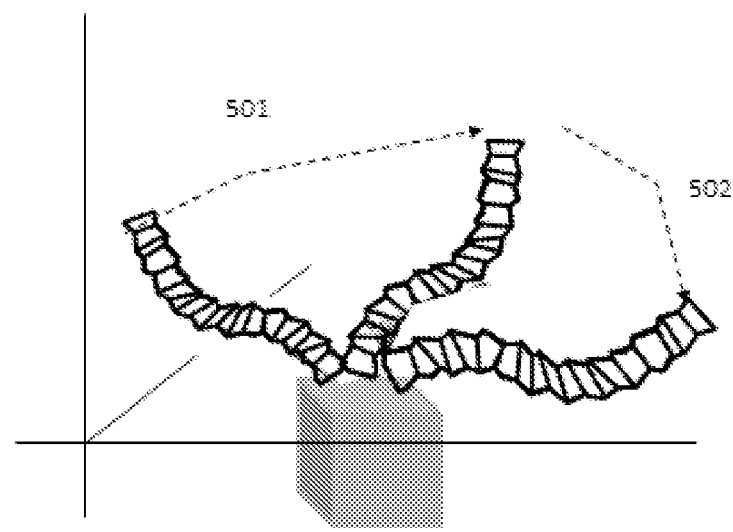
FIG. 5 shows how a flexible, ribbed hose may be maneuvered from one position, to a second position and then to a third position.

As shown in FIG. 5, the flexible, ribbed hose can be moved from a first position to a second position (501), and then from a second position to the third position (502). Running axially within the hose are positioning elements (not shown) that can be extended, retracted and bowed allowing positioning of the hose in three dimensions within an air volume zone.

Figure 6:
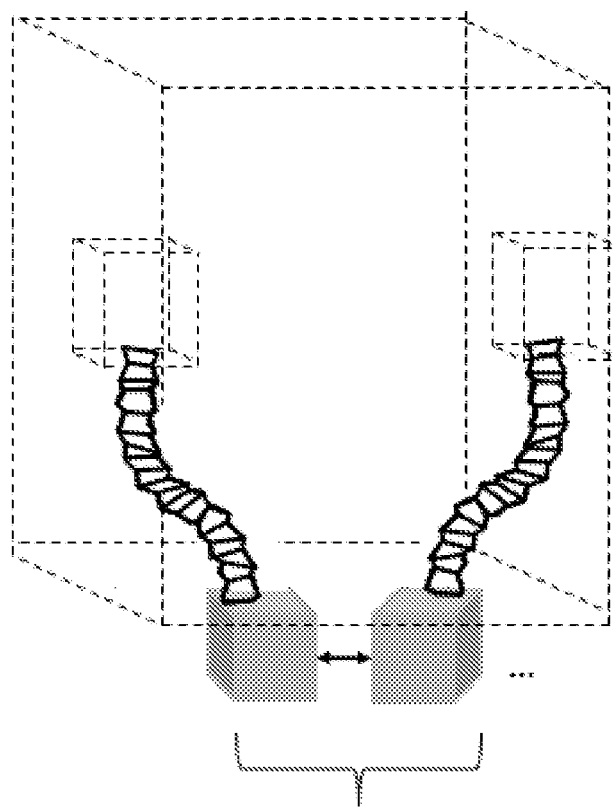
FIG. 6 shows how multiple systems may be linked together to provide parallel operation within an air volume zone.

As shown in FIG. 6, to reduce the time of the sampling, testing and filtering process, two or more invention systems (601) may be linked and positioned within the same air volume zone thereby providing parallel sampling, testing and filtering.

Figure 7:
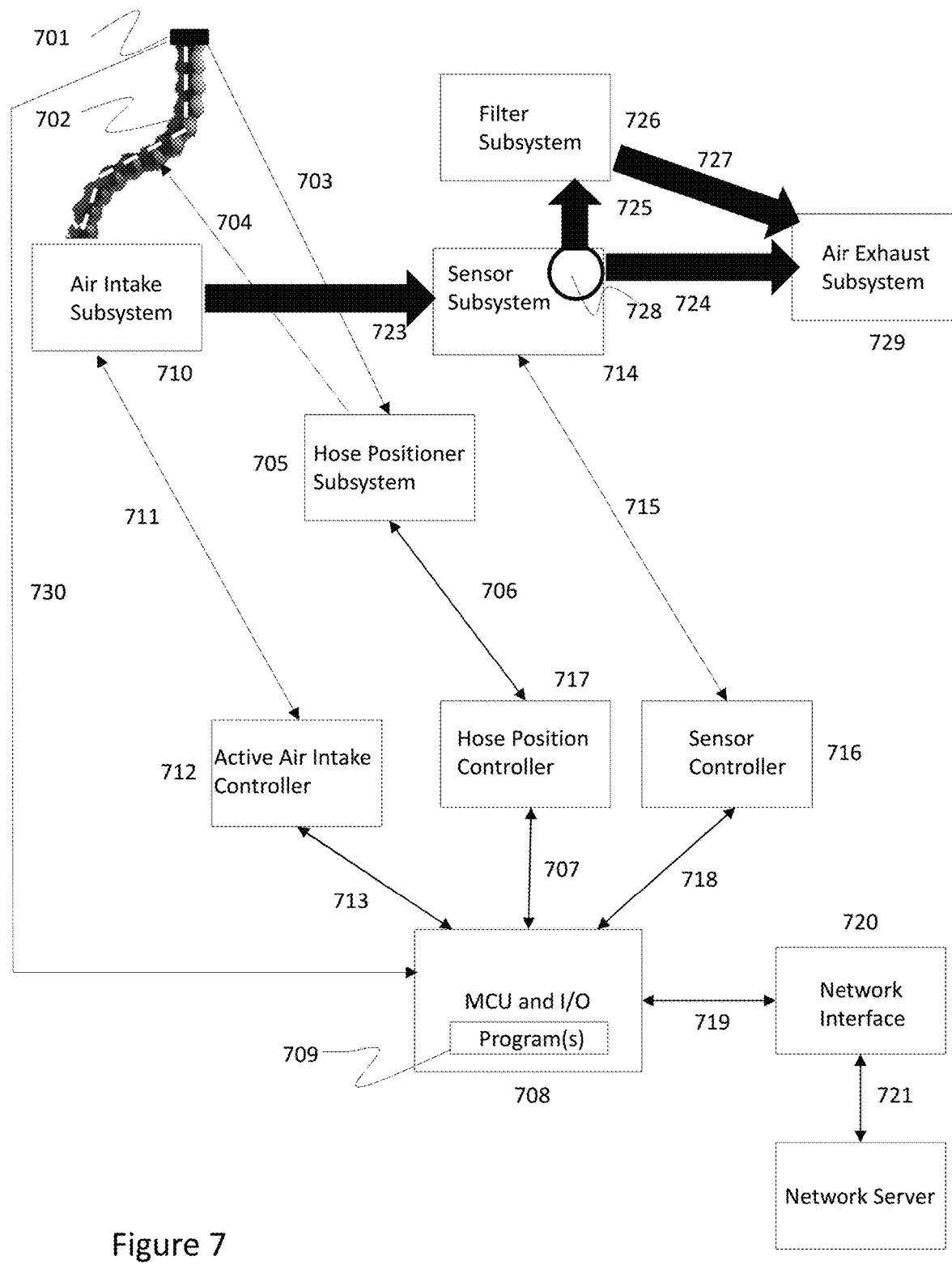
FIG. 7 depicts an embodiment of the system and all its subsystems.

FIG. 7 illustrates one embodiment of the invention system wherein a flexible, ribbed hose, with position-detection device, and environmental sensors (e.g. heat, smoke, sound) (701) located at its tip, has its other end interfaced to an air intake subsystem's input air port. The hose's position is controlled by a hose position controller's (717) command conveyed to a hose positioner subsystem (705) over a bidirectional data path (706) and a command signal path (704). Hose position commands cause positioning elements (702) to extend, or retract, or bow so as to position the hose tip in a selected sub-volume position. A closed-loop control is provided by data from the position-detection device (701) conveyed to the hose positioner subsystem (705) over data path 703. Prompted by an "in position" signal from a microcontroller subsystem (708) under program (709) control, conveyed to an air intake controller (712) over bidirectional data path (713), the air intake controller conveys a command over path 711 to the air intake subsystem (710) that starts an electric pump causing air to enter the hose tip, flow into the air intake system and through an air duct (723) into a sensor subsystem (714). The sensor subsystem allows the air to pass over a sensor operative to detect particulate, or gaseous, or biologic pathogen contaminants. The sensor system (714) conveys test status data to a sensor controller (716) over path 715, and the sensor controller (716) conveys the test status data to the microcontroller subsystem (708) over path 718. Essentially, concurrently, if the sensor test is positive for contaminants, the sensor controller (716) conveys a command over path 715 to the sensor subsystem (714) to change its valve (728) state such that air flows through air duct 725 into filter subsystem (726). Filtered air from the filter subsystem (726) is conveyed via duct 727 to the air exhaust system (729). If test results show no contaminants, the valve default position remains such that air flows through air duct 724 into air exhaust subsystem (729). The microcontroller subsystem (708) comprises a microcontroller, RAM memory, program memory and input-output (not shown). It interfaces with the air intake controller via bidirectional path 713, with hose position controller (717) via bidirectional path (707) and with sensor controller (716) via bidirectional path 718. Each invention system is capable of executing its own embedded control program (709). In addition, the microcontroller subsystem and network interface (720) communicate via bidirectional path 719, and the network interface (720) interfaces with a server (722) via bidirectional path 721. This enables the individual systems to become part of a coordinated effort by multiple systems, in the same or multiple air volume zones to be redirected to specific sub-volume positions so as to optimize sampling, testing and filtering where multiple instances of contamination are detected. In addition, the individual system's data is collected by the server to provide ongoing, real-time logging of process operation and findings. In addition, environmental sensors (701) located at the tip of the ribbed hose may provide heat, smoke and sound detection wherein signals associated with such detection are conveyed directly via path 730 to the microcontroller subsystem, and via the network interface, to the server. These detections may serve as an immediate indication of something unanticipated which could trigger an interrupt routine comprising alarms and evacuation directives allowing system sampling, sensing and filtering to proceed while mitigating any danger to those occupants in a facility.

Figure 8:
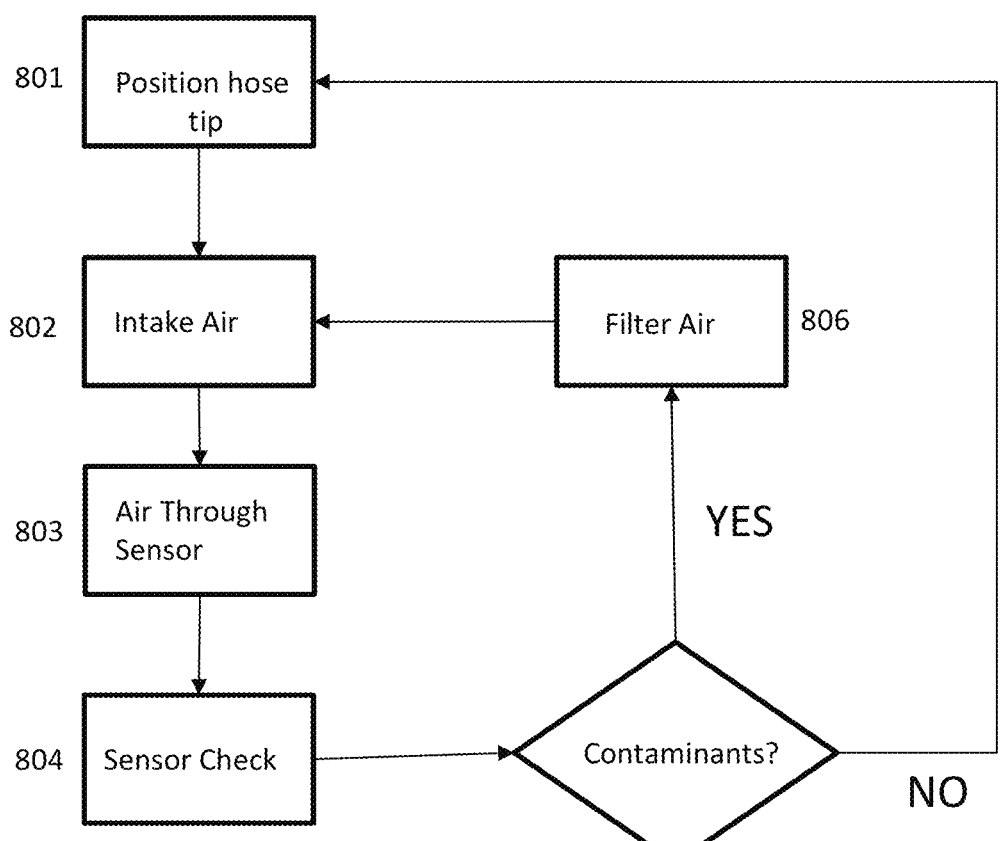
FIG. 8 shows an exemplary flow of functional sequences the underlie the operation of the system.

As shown in FIG. 8, the flow diagram depicts a method of use wherein the hose tip is positioned (801), the air in the sub-volume is taken in (802), the air passes through the sensor subsystem (803), the air is checked for contaminants (804), if no contaminants, the hose is repositioned, and if there are contaminants, the air is diverted to the filter and filtered (806) then with hose in same position, air continues to be sampled and tested until negative for contaminants.

The drawings and descriptions are meant to be exemplary and should not be read as limiting the scope of the invention. The flexible, ribbed hose can be made of plastic or metal. The hose's length is determined by the dimensions of the air volume zone to be sampled. The air flow through the hose and following systems is determined by the time requirements for sampling a selected sub-volume. The sensor subsystem's sensors are specific to detecting particulate, gaseous or biologic pathogen contamination. Similarly, the filter subsystem's filters are specific to filtering particulate, gaseous or pathogenic contaminants. The containment portion of the system may be fixed in place or may contain wheels and propulsion mechanisms, as well as sensors that prevent the system from proceeding over the edge of a surface or colliding with another object on that surface, thus allowing it to move in conjunction with the flexible, ribbed hose so as to reduce positioning time. The unidirectional and bidirectional signal paths for conveying commands and data may be conductive (e.g. wires) or wireless. Multiple bidirectional paths may be combined into one or more bus-type paths to which multiple subsystems are interfaced. Power is provided to the subsystems (not shown) using self-contained power source (e.g. battery) or via a power cord connected to a utility outlet. Where self-contained sources are used, low-battery-charge condition would be sensed and a message sent to initiate a replacement or charging sequence.

What is claimed is:

1. A system comprising:
  a flexible, ribbed hose;
  a hose-positioner subsystem operative to receive position data from a position-detection device on an open end of said flexible, ribbed hose, and to convey position-control commands to positioning elements within said flexible ribbed hose, wherein said positioning elements can expand, contract and bow in response to said position-control commands; said position-control commands are a result of processing done by a microcontroller subsystem based on said position data and programmed algorithms; and said position-control commands are conveyed to a hose-position controller by said microcontroller subsystem and by said hose-position controller to said hose-positioner subsystem;
  an air intake subsystem comprising:
    an incoming air port;
    an air exhaust port;
    an electric pump operative to draw air in through said incoming air port and blow air out through said air exhaust port;
  a first air duct operative to convey air from said air exhaust port to a sensed-air input port;
  a sensor subsystem comprising a sensing device operative to detect the presence of contaminants in air entering said sensed-air input port and to convey sensed-air results data to a sensor controller;

wherein said sensor controller is operative to receive said sensed-air results data, to convey said sensed air results data to said microcontroller subsystem, and to convey valve-control commands to said sensor subsystem;

a valve operative to conditionally direct air flow exiting said sensor subsystem to a filter subsystem or an air exhaust subsystem, based upon said sensed-air results data, wherein:

if contaminants are present, said air flow is directed to said filter subsystem via a second air duct;

if contaminants are not present, said air flow is directed to said air exhaust subsystem via a third air duct;

said filter subsystem comprising:

one or a plurality of filters operative to remove contaminants from air flowing through said filter subsystem;

a fourth air duct via which post-filtered air exiting said filter subsystem is conveyed to said air exhaust subsystem;

said air exhaust subsystem being operative to convey air flowing in from said third air duct or said fourth air duct to an air exhaust subsystem exhaust port;

an active air intake controller operative to receive electric pump on and off commands from said microcontroller subsystem and to convey said electric pump on and off commands to said air intake subsystem;

said microcontroller subsystem comprising:

a microcontroller;
random-access memory;
stored program memory comprising said programmed algorithms; and
an input-output system;

a first set of bidirectional data paths operative to convey data between said microcontroller subsystem and said air intake controller, said hose position controller, said sensor controller, and a network interface;

wherein said network interface is operative to convey commands and other data between said microcontroller subsystem and a network server;

a bidirectional network data path operative to convey said commands and other data from said network server; and a power supply subsystem operative to provide operating power to:

said air intake subsystem;
said active air intake controller;
said hose positioner subsystem;
said hose position controller;
said sensor subsystem;
said sensor controller;
said network interface; and
said microcontroller subsystem.

2. A system as in claim 1 wherein said sensor subsystem comprises one or more sensors operative to detect particulate contaminants.

3. A system as in claim 1 wherein said sensor subsystem comprises one or more sensors operative to detect gaseous atomic or molecular contaminants.

4. A system as in claim 1 wherein said sensor subsystem comprises one or more sensors operative to detect biologic pathogen contaminants.

5. A system as in claim 2 wherein said one or a plurality of filters are operative to remove said particulate contaminants.

6. A system as in claim 3 wherein said one or a plurality of filters are operative to remove said gaseous atomic or molecular contaminants.

7. A system as in claim 4 wherein said one or a plurality of filters are operative to remove said biologic pathogen contaminants.

8. A system as in claim 1 wherein said power supply subsystem is powered by self-contained replaceable batteries.

9. A system as in claim 1 wherein said power supply subsystem is powered by a utility power source via a wired interface.

10. A method comprising:

positioning an air intake hose to a first one of several predetermined positions;

turning on an air intake electric pump once said intake hose is in said first one of several predetermined positions;

sensing the air taken in for contaminants while keeping said hose in said first one of several predetermined positions; and determining if the sensed air contains said contaminants wherein:

if said contaminants are detected then diverting air flow through a filter subsystem while keeping said air intake hose in said first one of several predetermined positions until sensor results are negative for contaminants; and if no contaminants are detected, then moving said air intake hose to a new predetermined position.

* * * * *